US006848322B2

(12) United States Patent
Scarborough

(10) Patent No.: US 6,848,322 B2
(45) Date of Patent: Feb. 1, 2005

(54) APPARATUS AND METHOD FOR TESTING WELD INTEGRITY

(75) Inventor: Randall L. Scarborough, Carencrow, LA (US)

(73) Assignee: S & H Fabrication, Inc., Scott, LA (US)

( * ) Notice: Subject to any disclaimer, the term of this patent is extended or adjusted under 35 U.S.C. 154(b) by 0 days.

(21) Appl. No.: 10/365,105

(22) Filed: Feb. 12, 2003

(65) Prior Publication Data

US 2004/0154408 A1 Aug. 12, 2004

(51) Int. Cl.[7] .................................................. G01N 3/20
(52) U.S. Cl. ...................................................... 73/850
(58) Field of Search ........................ 73/850, 816, 820, 73/837

(56) References Cited

U.S. PATENT DOCUMENTS

| | | | | |
|---|---|---|---|---|
| 2,424,177 A | * | 7/1947 | Lawshe et al. ............... | 73/828 |
| 3,142,980 A | * | 8/1964 | Anderson ..................... | 73/834 |
| 3,548,646 A | * | 12/1970 | Holman ....................... | 73/795 |
| 3,942,368 A | * | 3/1976 | Hoyt ........................... | 73/842 |
| 3,994,158 A | * | 11/1976 | Weinhold ..................... | 73/798 |
| 4,249,062 A | * | 2/1981 | Hozumi et al. ........ | 219/124.34 |
| 4,478,086 A | * | 10/1984 | Gram .......................... | 73/781 |
| 4,520,655 A | * | 6/1985 | Owens ......................... | 73/46 |
| 4,610,166 A | * | 9/1986 | Elder et al. .................. | 73/818 |
| 5,212,654 A | * | 5/1993 | Deuar ......................... | 702/43 |

* cited by examiner

*Primary Examiner*—Max Noori
(74) *Attorney, Agent, or Firm*—The Matthews Firm

(57) ABSTRACT

An apparatus and method for testing weld integrity is disclosed which is portable, self-contained, adaptable for field use in most locations, and can verify the integrity of attachment welds. The testing apparatus includes a cylinder or cylinders, attachable to the desired object to be tested on one end and to a cross bar on the other end, support beam or beams which, along with the cylinder or cylinders, support the test apparatus, a supply for pressurized fluid, and a control manifold for flow direction and pressure measurement. The pressurized fluid moves the cylinder shaft creating a load on the test piece. As the fluid pressure increases the cylinder shafts extract or retract and exert a required load on the test piece. The test piece is then inspected for breakage or damage such as deformation or attachment weld cracking.

21 Claims, 13 Drawing Sheets

APPARATUS AND METHOD FOR TESTING WELD INTEGRITY

AREA OF TECHNOLOGY

The present apparatus relates, generally, to non-destructive testing of weld integrity and strength in the attachment weld of pad eyes and other lifting lugs.

BACKGROUND OF INVENTION

Presently, the weld integrity of pad eye or other lifting lug welds are only tested by x-rays or liquid penetrant. This testing is at best random and cannot insure the safety or reliability of the pad eyes especially after many cycles. The failure of the pad eyes can cause equipment damage and destruction as well as compromise the safety of workers and by-standers. In particular, when drill string piping is off loaded, from a barge or supply boat, the failure of the pad eyes does cause the loss of human life due to the extreme weight of the pipe and its uncontrolled fall.

Pad eyes and lifting lugs are primarily used as an attachment point for any rigging employed to hoist, transport, or secure heavy equipment. These pad eyes are typically welded either to the equipment or to some device on which the equipment is transported on. The strength of these welds cannot be easily tested after they have been manufactured. Usually, the only indication of weakness is discovered upon the complete failure of the attachment weld.

Currently, there are similar approaches to the present device disclosed in other patents. However, there is no prior art for the method or apparatus for testing the pad eye welds. U.S. Pat. No. 4,676,110 discloses a fatigue testing apparatus. However, this apparatus utilizes a method of destructive testing which would render the pad eye useless. Other prior art for pull testing is disclosed in U.S. Pat. Nos. 5,844,142 and 5,918,284. However, these systems are not portable, are not for larger loads, and are only intended for testing the products during manufacturing. These systems are also used to test the strength for one time use only products, such as surgical suture and needles. The pad eye welds must withstand a vast number of loading cycles, with a varied amount of load, throughout their useful life.

There are other prior art testing tools such as disclosed in U.S. Pat. No. 6,186,011 B1 which tests the failure modes of spot welds on sheet metal. Another testing tool disclosed in U.S. Pat. No. 6,216,531 B1, tests the shear strength of adhesive bonded materials. However, both of these inventions are based on pre-manufacture testing, do not consider cyclic loading over the useful life of the product, and cannot be adapted for portability. These testing tools also cannot be adapted to perform testing of finished products or to test the weld integrity before each use.

It is thus a desire to have a testing apparatus which is portable and can quickly and accurately check the integrity of a pad eye and its attachment weld before each field use. The desired apparatus should be portable, self-contained, easily transportable, and environmentally safe in order to test the pad eye welds at almost any location. This testing device should be capable of being hydraulically operated as well as by other available pressurized fluid sources. This device could consist of one or multiple pressurized fluid cylinders depending on the required test loads and the configuration of the apparatus. The effective area of the cylinder piston and the pressure applied to the cylinder would determine the capacity of the apparatus. The fluid pressure is preferably supplied by a hand pump for currently optimum portability; however, other types of pumps could be utilized. A flow manifold would be needed to control the flow direction as well as measure the pressure applied to the cylinder(s). One end of the cylinder(s) would be attached to the same base as is the pad eye or attached to its own base plate. The other end is attached to a cross bar, bridge plate, or similarly functioning member. The cross bar, bridge plate, or similarly functioning member could be further supported by either cylinders or support beams.

BRIEF DESCRIPTION OF THE DRAWINGS

For a further understanding of the nature of the present device, reference should be had to the following detailed description, taken in conjunction with the accompanying drawings, in which like elements are given the same or analogous reference numbers and wherein.

DETAILED DESCRIPTION OF AN EMBODIMENT OF THE PRESENT APPARATUS

Figure 1:
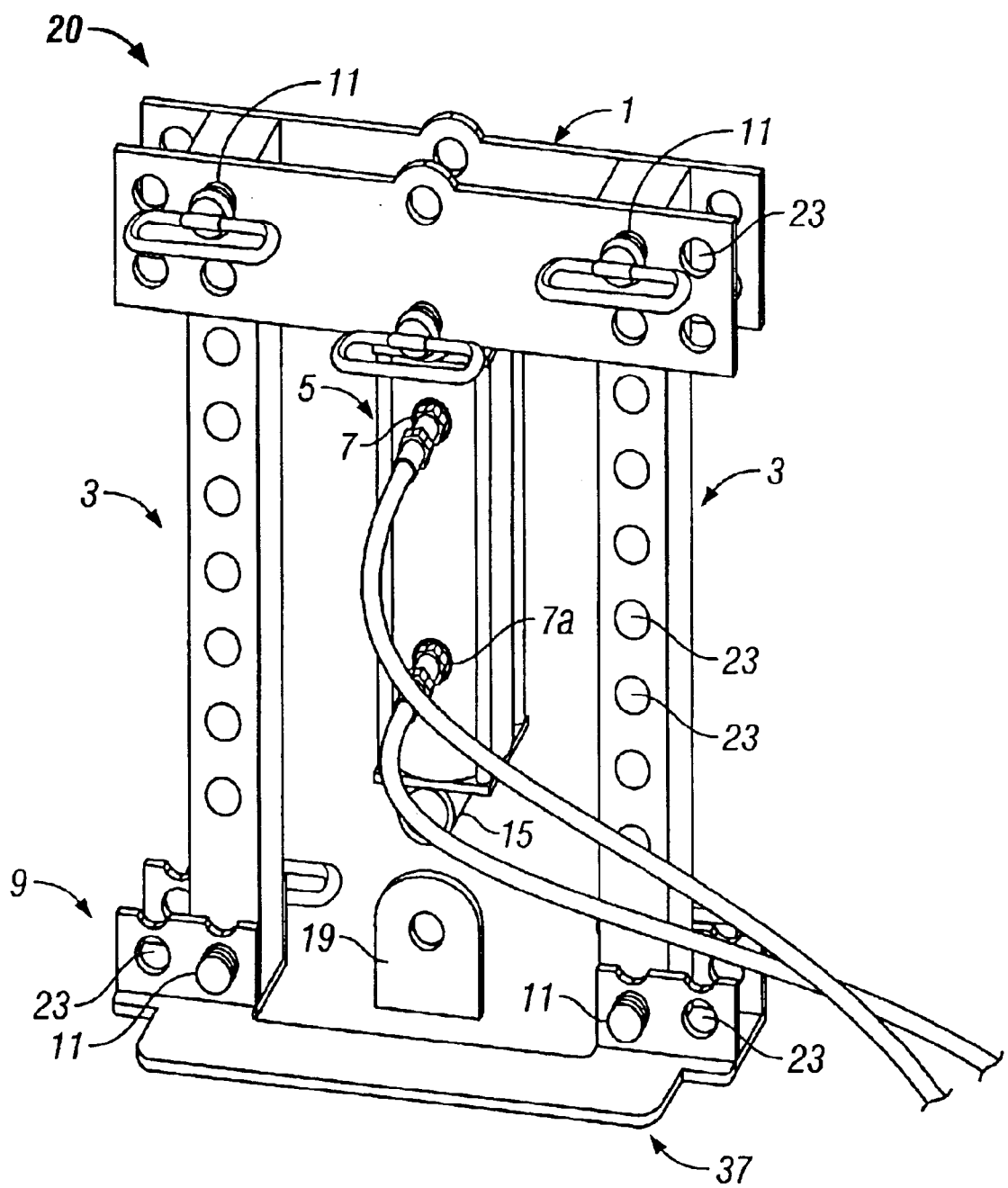
FIG. 1 is a front view assembly drawing of a preferred form of the testing apparatus 20.
Figure 2:
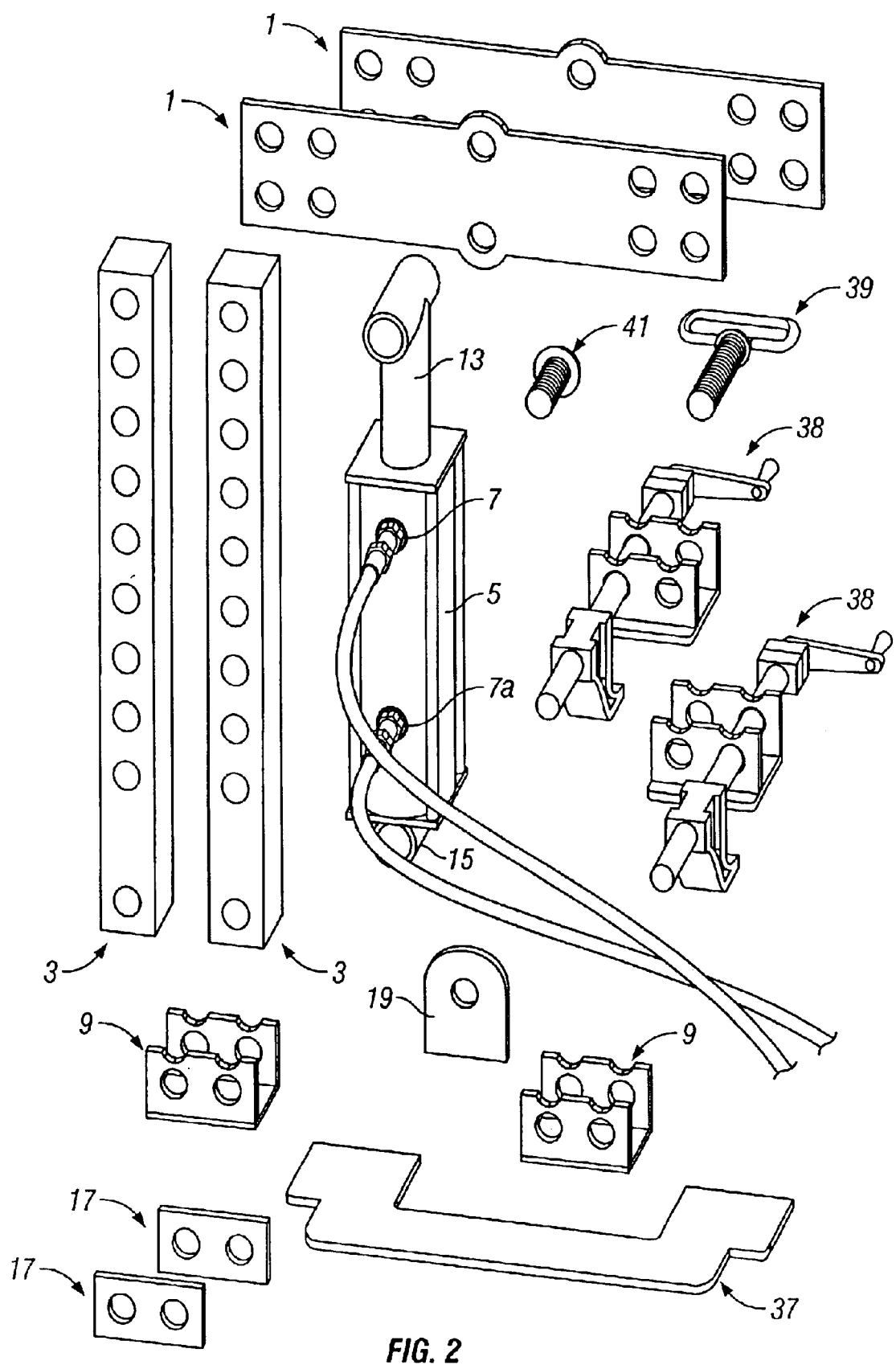
FIG. 2 is a view of FIG. 1 in its disassembled state.

First Embodiment (FIG. 1 and FIG. 2)

FIG. 1 is an assembly drawing of the present device. FIG. 2 shows the individual components of the testing apparatus 20 which includes the cylinder 5, two bridge plates 1, two support beams 3, one being the right side beam and one being the left side beam, two footings 9 comprised of a right side footing and a left side footing, and two attachment plates 17.

It should be appreciated that the footings 9 and the attachment plates 17 are an illustrative method of attaching the apparatus to the pad eye 19 or lifting lug. Other ways of attachment, which provide adequate support and connection can be employed without departing from the scope thereof. The test apparatus can be mounted to a base plate 37 in order to provide support for the test apparatus, it can be used without the base plate 37 and attached via clamps 38 or other suitable method directly to the base support structure to which the pad eye 19, the lifting lug, or other lifting connection is attached to.

Figure 7:
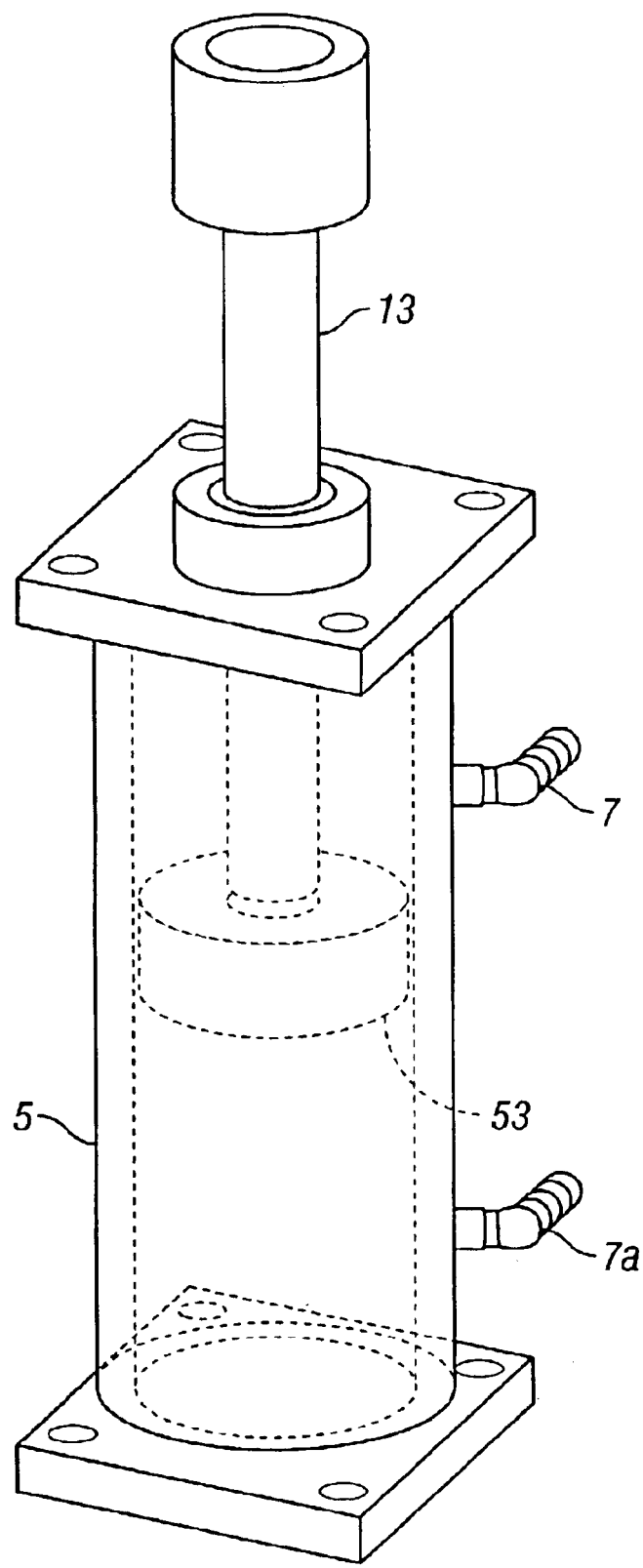
FIG. 7 is a simplified cross sectional representation of the cylinder depicted in FIGS. 1, 2, 3, and 4.

As shown in FIG. 1 and FIG. 2, the cylinder 5 is comprised of a shaft 13 on the topside of the cylinder, an upper 7 and lower 7A cylinder fitting, and a bottom adaptor 8. The internal portion of the cylinder, FIG. 7, is well known to those in the art and typically consists of one or more pistons 53 and o-rings or seals. The said piston 53 is attached to the shaft 13 and will typically move upward, extending the cylinder shaft 13 as pressure is applied through the lower cylinder fitting 7A. When the pressurized fluid is applied through the upper cylinder fitting 7, the piston moves downward and the cylinder shaft 13 retracts. Both the cylinder shaft 13 and the bottom adaptor 15 are adapted to allow connection to a mating part preferably utilizing a pin connection. It should be appreciated that although the present device contemplates primarily pinned connections, other methods of attachment can also be used. Examples of such attachment include, but are not limited to: various threaded fasteners, taper pins, welding, and the like. The figures illustratively show two types of pins 39, 41. However, these pins 39, 41 can be interchanged as well as be substituted by a variety of other attachment methods as mentioned above. The cylinder shaft 13 is sandwiched between and connected, by a pin 41, to the two bridge plates 1. The bottom adaptor 15 is connected by a pin 41 and sandwiched between the attachment plates 17. For the preferred embodiment of the present apparatus, pressure containing hoses are connected to the upper 7 and lower 7A cylinder fittings.

Each of the two bridge plates 1 are preferably substantially identical flat rectangular bars made of steel or a material with similar strength properties. These said bridge plates 1 have a plurality of holes 23 which are used for the fixed connections between the two bridge plates 1 and the cylinder shaft 13 and the two support beams 3. It should be appreciated that the hole 23 diameter and consequently the diameter of the pin 41 vary in size depending on the load which will be tested and are typically sized by calculation based on the maximum load contemplated. Preferably, there is a plurality of holes 23 located on the right and left lengthwise ends of the bridge plate 1 and also located substantially symmetrically around the lengthwise and widthwise centers of the said bridge plate 1. Preferably, said holes 23, located on the right and left lengthwise ends, should be substantially symmetrically located at each end of the bridge plates. Preferably, said holes 23, at each end of said bridge plate 1, are substantially symmetrically located with respect to said bridge plate 1 and each other. The holes 23 located approximately midway of both the lengthwise and widthwise centers of said bridge plates 1 are preferably substantially symmetrically located at said midway point. The multiple holes 23 are used for allowing vertical and horizontal adjustment of the test apparatus. The cylinder shaft 13 is preferably fixedly attached at substantially the lengthwise midpoint of the bridge plate 1 by pin 41. The two bridge plates 1 are fixedly attached at opposing ends, left and right side, and to the outside face of the two support beams 3 by pin 41.

The two support beams 3 are preferably hollow rectangular beams made of steel or a material with similar strength properties. These said support beams 3 have a plurality of holes 23 on all four faces of the rectangular beam which are used for the fixed connections between the two support beams 3 and the two bridge plates 1 and the two footings 9. It should be appreciated that the hole 23 diameter and consequently the diameter of the pin 41 vary in size depending on the load which will be tested and are typically sized by calculation based on the maximum load contemplated. Preferably, the holes 23, on each face of the support beams 3, are substantially centered lengthwise on each face of the support beam 3 and are substantially symmetrically spaced from the top of said support beam 3. The multiple holes 23 are used for allowing vertical and horizontal adjustment of the testing apparatus. The bottom end of the two support beams 3 has a hole on each of the four faces. Preferably, the said holes 23 are substantially symmetrically located on the lengthwise center line of each face of the said support beam 3. As described above and shown in FIG. 1, the support beams 3 are fixedly attached near the top end of said support beam 3 sandwiched between the two bridge plates 1 and fixedly attached preferably utilizing the pin 41. The bottom end, of each said support beam 3, is preferably fixedly attached to the two footings 9 by pin 41.

The two footings 9 are preferably comprised of a steel, or a material with similar strength properties, channel bar. Preferably, the two channel sides have matching holes 23 on each face. Preferably, said hole diameters are substantially symmetrically centered relative to the said channel bar height and substantially symmetrically spaced between the respective holes centers on each channel wall face. The two footings 9 will preferably be attached by welding to the test apparatus base plate 37 or attached by clamps to the pad eye base plate 21. Preferably, the two footings 9 are substantially horizontally and symmetrically centered on each side of the pad eye 19. This said placement, of the two footings 9, is assured through the substantially symmetric connection of the support beams 3 to bridge plate 1. This said positioning insures that the testing apparatus will provide an approximately equal upward force on the pad eye 19.

The two attachment plates 17 are comprised of two substantially identical pieces of flat steel, or a material with similar strength properties, bar. The said attachment plates 17 have a plurality of holes 23. The hole 23 diameters are substantially centered along the lengthwise centerline of the flat face of the attachment plates 17. The said holes 23 are further substantially symmetrically located at opposing lengthwise ends of the said attachment plates 17. The adjustment plate 17 is fixedly attached on the upper end, by pin 41, to the end of the bottom adaptor 15. The said bottom adaptor 15 is fixedly attached, by pin 41, pinned between the two attachment plates 17. The lower end of said attachment plates 17 is attached to the pad eye 19 by pin 39. The pad eye 19 is sandwiched between the two attachment plates.

Figure 8:
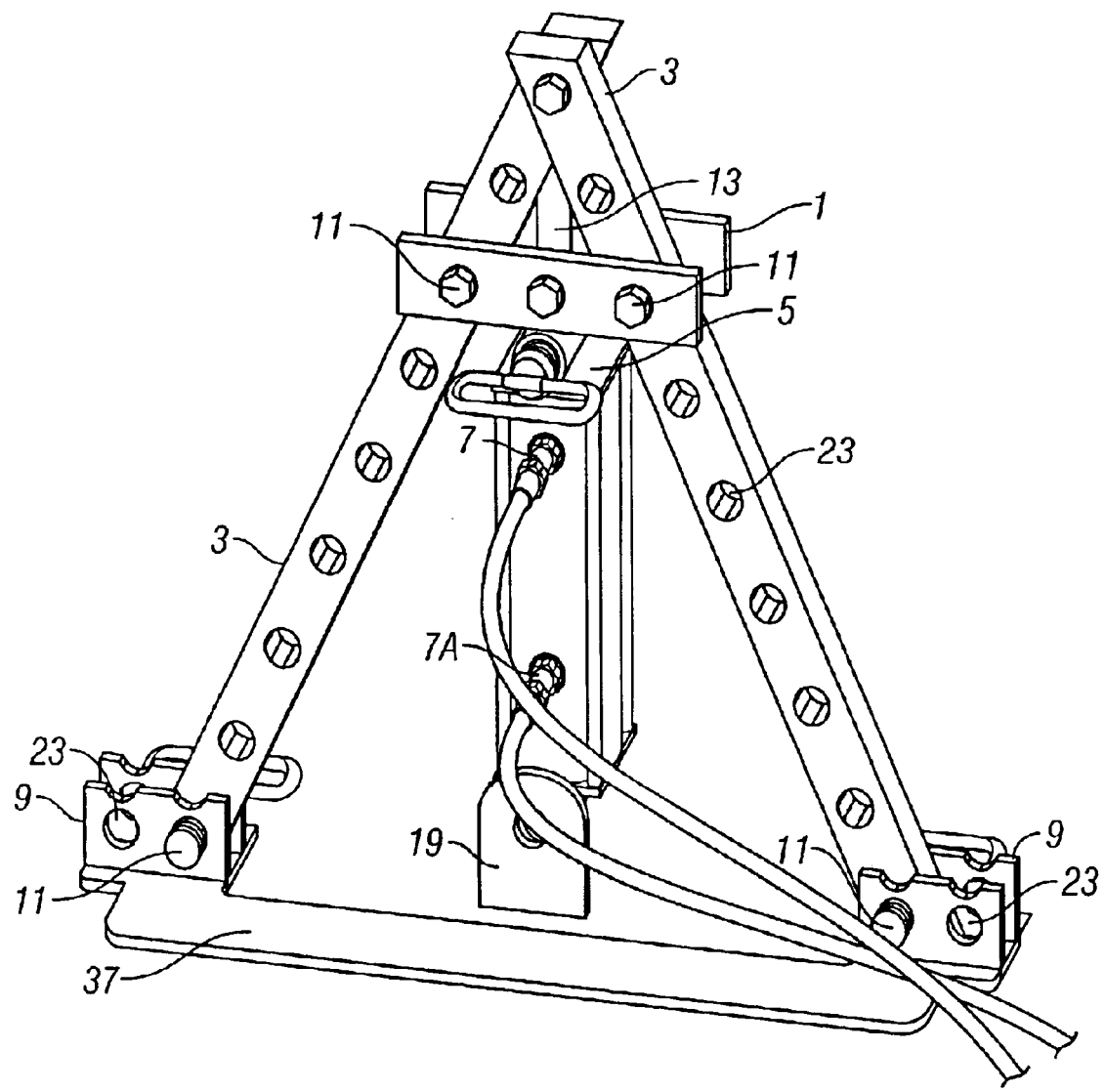
FIG. 8 is a front view assembly drawing of an alternative embodiment of the testing apparatus.
Figure 8A:
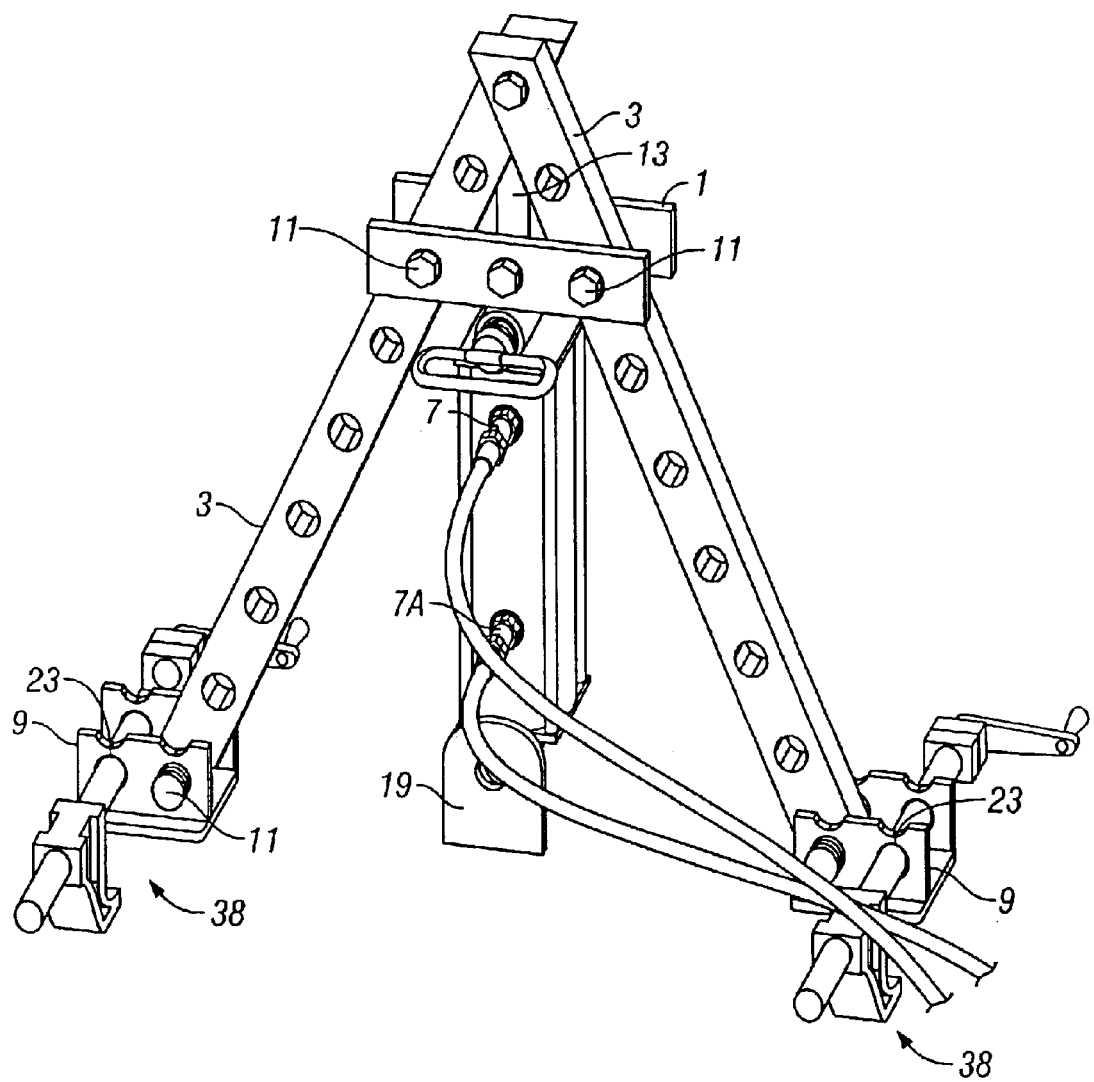
FIG. 8A is another embodiment of FIG. 8 illustrating the option of attachment, of the present apparatus, to the device to be tested, by clamps.

An alternative embodiment of this structure, shown in FIGS. 8 and 8A, could be an A-frame wherein the cylinder is attached to a crossbar or the apex of the A-frame.

Figure 3:
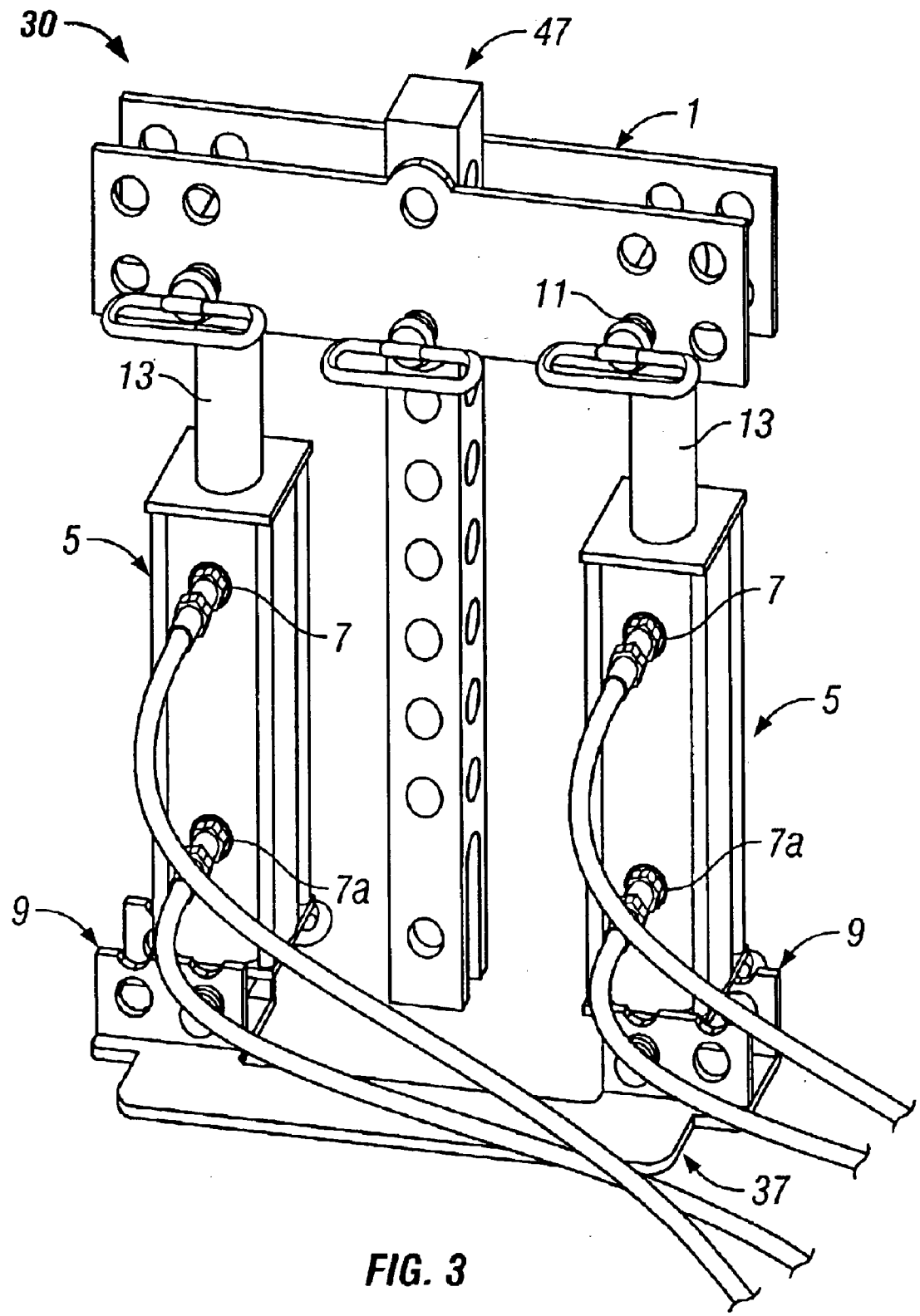
FIG. 3 is a front view assembly drawing of an additional embodiment of the testing apparatus.
Figure 4:
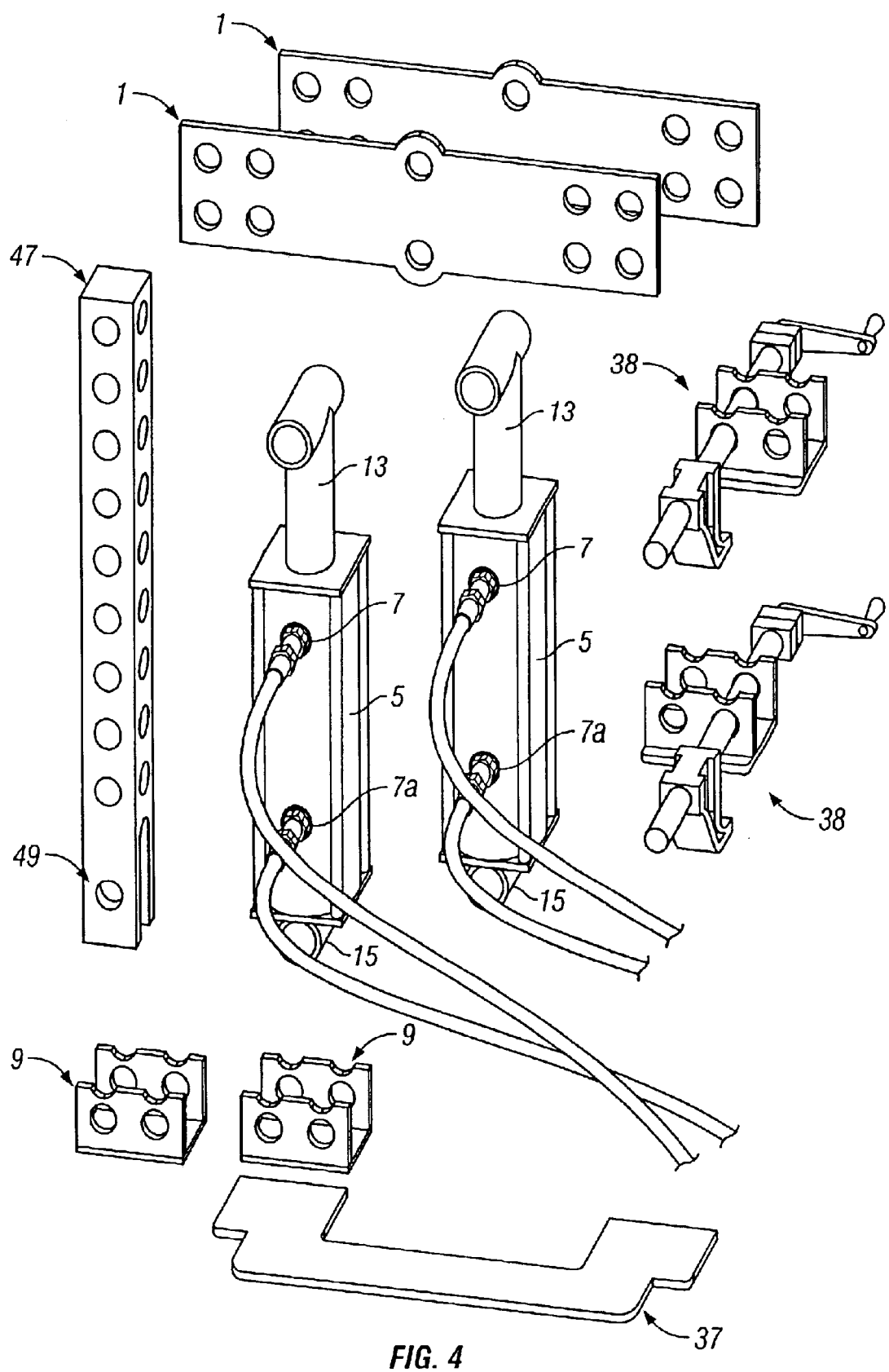
FIG. 4 is a front view of a FIG. 3 in its disassembled state.

Second Embodiment (FIG. 3 and FIG. 4)

FIG. 3 is an assembly drawing of an additional embodiment of the present apparatus. FIG. 4 shows the individual components of said additional embodiment 30 which is preferably comprised of the two cylinders 5, one being the right side cylinder and one being the left side cylinder, two bridge plates 1, the support beam 47, and two footings 9 comprised of a right side footing and a left side footing.

It should be appreciated that the footings 9 and the attachment plates 17 are an illustrative method of attaching the apparatus to the pad eye 19 or lifting lug. Other ways of attachment, which provide adequate support and connection can be employed without departing from the scope thereof. The test apparatus can be mounted to a base plate 37 in order to provide support for the test apparatus, it can be used without the base plate 37 and attached via clamps 38 or other suitable method directly to the base support structure to which the pad eye 19, lifting lug, or other lifting connection is attached to.

Figure 3A:
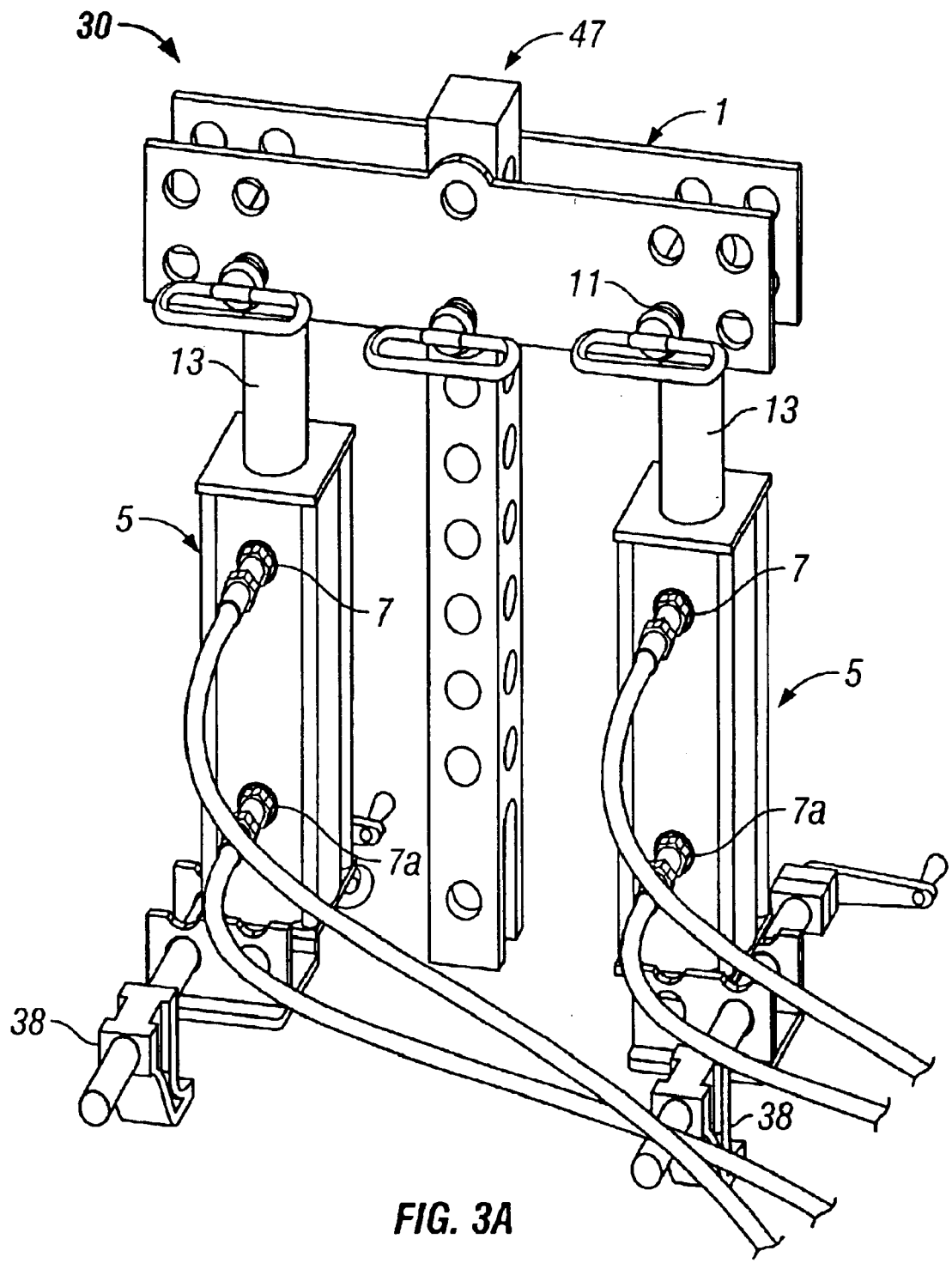
FIG. 3A is another embodiment of FIG. 3 illustrating the option of attachment, of the present apparatus, to the device to be tested, by clamps.

As shown in FIG. 3, FIG. 3A, and FIG. 4, the two cylinders 5 are comprised of similar components as the cylinder 5 for the single cylinder apparatus. It should be appreciated that since the actual cylinder size may change according to the required load the components may also change in size. Both the cylinder shaft 13 and the bottom adaptor 15 are adapted to allow connection to mating parts preferably utilizing a pin connection. The cylinder shaft 13, of the right side cylinder 5 is fixedly attached by a pin 41 to the right end and in between the two bridge plates 1. The cylinder shaft 13, of the left side cylinder 5, is fixedly attached by a pin 41 to the left end and in between the bridge plates 1. The bottom adaptor 15, of the right cylinder 5, is fixedly attached, by a pin 41 to the right side footing 9. The bottom adaptor 15, of the left cylinder 5, is fixedly attached, by a pin 41 to the left side footing 9. It should be noted and appreciated by those in the art that the figures illustratively show two types of pins 39, 41. However, these pins 39, 41 can be interchanged as well as be substituted by a variety of other attachment methods as mentioned above. Both the right side and left side cylinders 5 are each fitted with two cylinder fittings 7 and 7A For the preferred utilization of the present device, pressure containing hoses are connected to the two cylinder fittings 7 and 7A on each cylinder 5.

Each of the two bridge plates 1 are preferably substantially identical flat rectangular bars made of steel or a material with similar strength properties. These said bridge plates have a plurality of holes 23 which are used for the fixed connections between the two bridge plates 1 and the cylinder shafts 13, of both cylinders 5, and the support beam 47. It should be appreciated that the hole 23 diameter and consequently the diameter of the pin 41 vary in size depending on the load which will be tested and are typically sized by calculation based on the maximum load contemplated. Preferably, there are a plurality of holes 23 located on the right and left lengthwise ends of the bridge plate 1 and also located substantially symmetrically around the lengthwise and widthwise centers of the said bridge plates 1. Preferably, the said holes 23, located on the right and left lengthwise ends, should be substantially symmetrically located at each end of the bridge plates 1. Preferably, said holes 23, at each end of said bridge plate 1, are substantially symmetrically located with respect to said bridge plate 1 and each other. The said holes 23 located approximately midway of both the lengthwise and widthwise centers of said bridge plates 1 are preferably substantially symmetrically located at said midway point. The multiple holes 23 are used for allowing vertical and horizontal adjustment of the test apparatus.

The support beam 47 is preferably a fabricated hollow rectangular beam, having a top side and a bottom side, in which two opposing bottom sides extend, in the lengthwise direction, beyond the other two opposing sides. The said opposing extended sides form a channel at the bottom end of the said support beam 47. The support beam 47 has a plurality of holes 23 on all four faces of the rectangular beam which are used for the fixed connections between the support beam 47 and the two bridge plates 1 and the two footings 9. It should be appreciated that the hole 23 diameter and consequently the diameter of the pin 41 vary in size depending on the load which will be tested and are typically sized by calculation based on the maximum load contemplated. Preferably, said holes 23, on each face of the support beam 47 are substantially centered lengthwise on each face of the support beam 47 and are preferably substantially symmetrically spaced from the top of said support beam 47. The multiple holes 23 are used for allowing vertical and horizontal adjustment of the testing apparatus. As shown in FIG. 4 and described above, the bottom channeled end of the support beam 47 has a hole on each face of the channel portion. These hole diameters are substantially symmetrically located in the center of each face of the said support beam bottom channel. As described above and shown in FIG. 3, the support beam 47 is fixedly attached near the top end of the beam sandwiched between the two bridge plates 1 preferably utilizing the pin 41. The bottom-channeled end of the support beam 47 is set over the pad eye 19. The said bottom channeled end of the support beam 47 is fixedly attached, preferably by pin 39, to the pad eye 19.

The two footings 9 are preferably comprised of a steel, or a material with similar strength properties, channel bar. Preferably, the two channel sides have matching holes 23 on each face. Preferably said hole diameters are substantially symmetrically centered relative to the said channel bar height and substantially symmetrically spaced between the respective hole centers on each channel wall face. The two footings 9 will preferably be attached by welding to the test apparatus base plate 37 or attached by clamps to the pad eye base plate 21. Preferably, the two footings 9 are substantially horizontally and symmetrically centered on each side of the pad eye 19. This said placement, of the two footings 9, is assured through the substantially symmetric connection of the right and left cylinders 5 to the bridge plate 1. This said positioning insures that the testing apparatus will provide an approximately equal upward force on the pad eye 19.

It should be understood that the frame could be modified in many aspects to achieve the substantially same function and substantially same result of the present device. For instance, the bridge plate 1 could be curved, angled, have additional members attached thereto, and the like. The structure and frame could be further modified using springs or other mechanisms to exert a tensioning force on the pad eye or lifting lug attachment weld.

Figure 5:
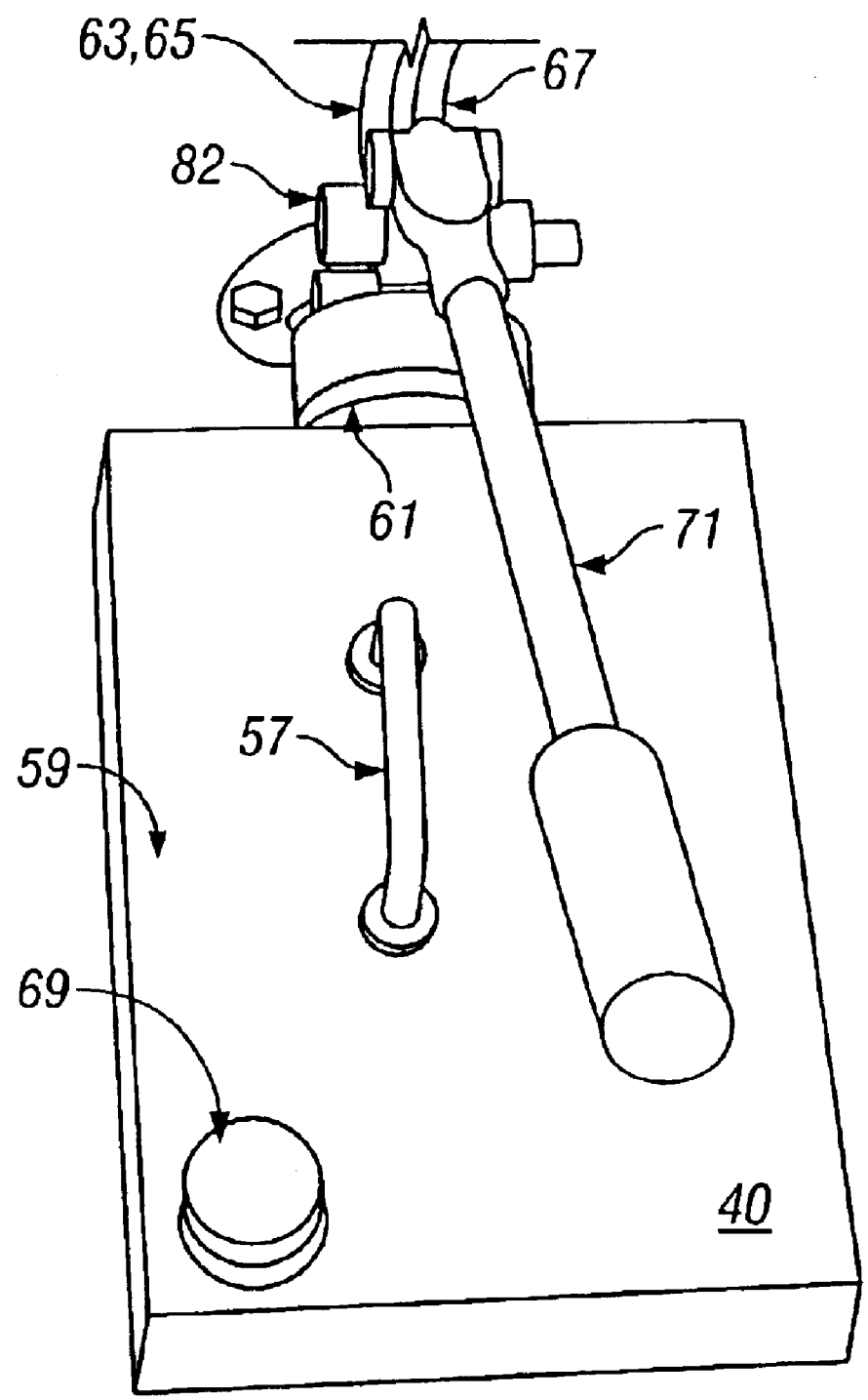
FIG. 5 is a pictorial view of the hand pump.
Figure 6:
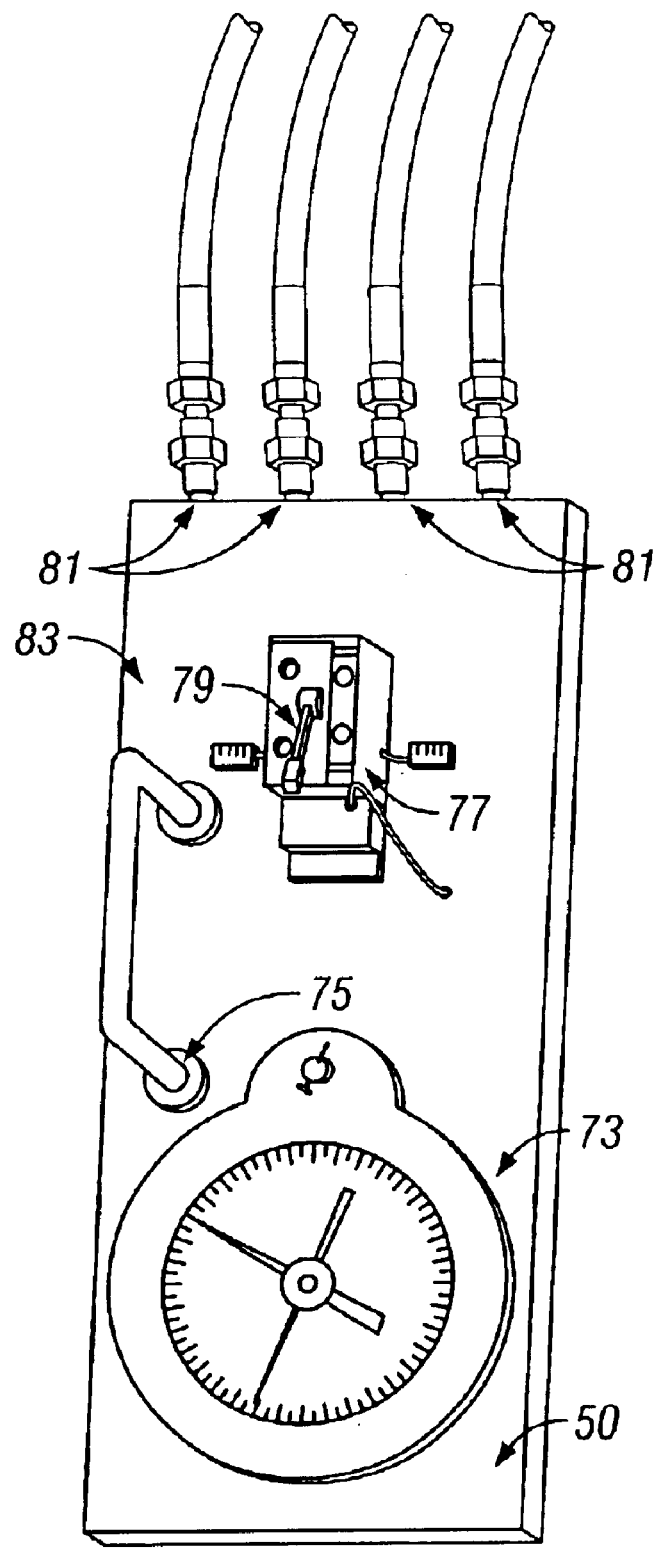
FIG. 6 is a pictorial view of the flow control manifold.

Operating Apparatus (FIG. 5 and FIG. 6)

Preferably, as shown in FIG. 5, the hand pump 40 is basically comprised of a reservoir 59, a carrying handle 57, a pump 61, the pumping handle 71, and a reservoir cap 69. It should be appreciated that although FIG. 5 shows a small typical hand pump, many varieties and combinations of pumps and fluid reservoirs or accumulators could be used to actuate this test apparatus. For the present device, a small hand pump is well suited for portability. If an adaptation of this apparatus were, for example, to be used in an industrial setting the pump may be otherwise powered, may be stationary, have larger reservoirs, use accumulators, use different fluids, or a multitude of different adaptations. For the present contemplated usage of this device, the cylinder shaft 13 is preferably actuated by a hand pump 40. The hand pump 40 is connected to the flow control manifold 50 by pressure containing hoses. The pump 61 is operated through the use of the pump handle 71.

As shown in FIG. 6, the flow control manifold 50 is comprised of a manifold 83, a pressure gauge 73, a directional valve 77, a directional lever 79, and a carrying handle 75. The direction of actuation and flow is preferably controlled by a directional valve 77. The directional valve 77 is further controlled by the rotational directional lever 79. Preferably the said directional lever can only be turned approximately ninety degrees in one direction and then approximately ninety degrees in the opposite direction. It should be appreciated, as with the hand pump above, that this is a typical manifold selected for the presently contemplated use of this device. However, as this apparatus is adapted for any variety of locations, the type, size, and configuration of the flow control manifold, including the type and configuration of the directional valve 77, as well as even the method of flow control itself may require substantial change. The flow control manifold 50 is preferably connected to the upper 7 and lower 7A cylinder fittings by means of pressure containing hoses. The flow control manifold 50 controls the direction of flow either into the lower cylinder fitting 7A, causing the cylinder shaft 13 to extend, or into the upper cylinder fitting 7 causing the cylinder shaft 13 to retract. The flow control manifold 50 also measures the pressure of the fluid. This pressure is shown on the mounted gauge but is also available to be displayed on a variety of recorders, computers, controllers, and the like.

In use, the present device can be transported in the disassembled condition to any location where some pad eye or lifting lug will be utilized or requires testing. One possible criterion for selecting a particular embodiment may be the required test load.

In use, prior to selecting the proper embodiment of the present device, the desired test load must be known. Typically, this value will be approximately 1.5 times greater than the rated load capacity of the pad eye or lifting lug. If such a rated load is not readily accessible, the test value would be approximately 1.5 times the weight that will be supported by the pad eye or lifting lug. It should be understood that the said multiplying factor of 1.5 is only a preferred safety factor; therefore, the value can vary depending on a user's experience or preference and should not be used as a limiting factor of the scope of the claimed apparatus. After determining the said load test value, the proper testing apparatus will be comprised of the correct size and number of cylinders 5 which can generate the required test load. The required test load is generated by the cylinder 5 and is produced by the combination of the pressure, produced by the hand pump 40 and measured by the manifold pressure gauge 73, acting over the effective area of the cylinder. The effective area of the cylinder is calculated based on the diameter of the piston 53 within the cylinder 5. As is known to those in the art, the effective area of the piston 53 can be obtained from the cylinder manufacturer. As is also well known to those in the art, the said effective area is multiplied by the pressure to predetermine the produced test load. After determining the test load as described above, selecting the cylinder size, as described above, and determining the required pressure to produce the said test load, as described above, the hand pump 40 is used to produce the required pressure.

Figure 1A:
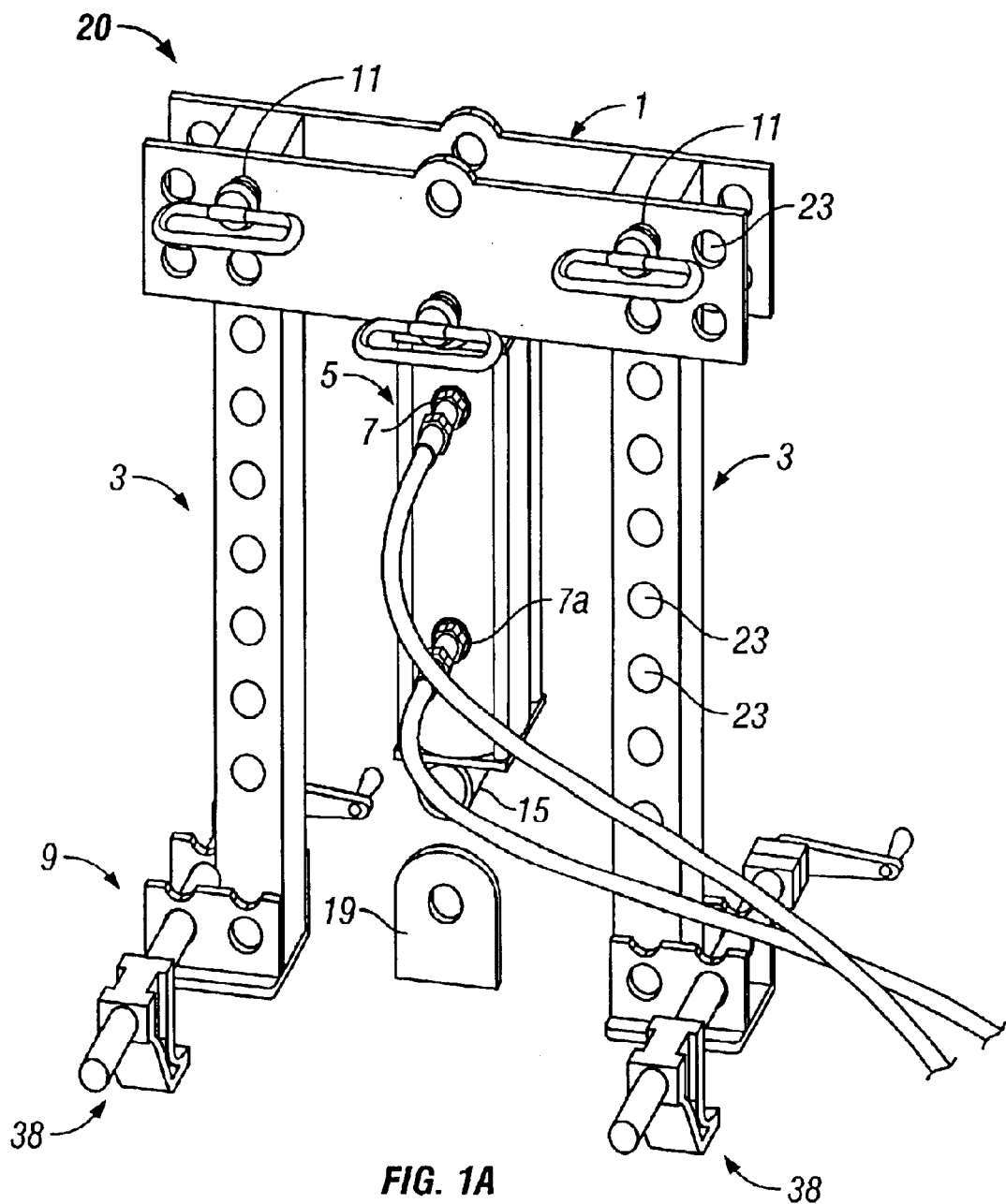
FIG. 1A is another embodiment of FIG. 1 illustrating the option of attachment, of the present apparatus, to the device to be tested, by clamps.

In use, the test apparatus is assembled as shown in FIGS. 1, 1A, 3, or 3A and discussed above. The apparatus is then connected to the pad eye 19, lifting lug, or other device to be tested. The connection, as shown in FIGS. 1 and 1A can include the use of attachment plates 17. In addition, a pressure containing hose is connected to each of the cylinder fittings 7 and 7A on the cylinders 5. The other end of each pressure containing hose is connected to the flow control manifold 50. The preferred embodiment utilizes "quick connect" connectors for the pressure containing fittings, however, other types of pressure containing fittings may be utilized. Preferably, the cylinder fittings 7 and 7A, the manifold fittings 81, and the pump fittings 73 are all male "quick connect" pressure containing fittings. Each pressure containing hose is preferably comprised of some length of hydraulic quality hose with a female "quick connect" fitting on each end. The pressure containing hose will have a pressure rating which exceeds the pressure required for the testing. Another set of the above described pressure containing hoses is connected between the flow control manifold 50 and the hand pump 40. It should be understood that the exact sequence and location of connection of the pressure containing hoses may vary depending on the version of the testing apparatus as well as the type and model of pump and flow control manifold. After the pressure containing hoses have been connected the pressurized system, comprised of the hoses and associated fittings, the hand pump 40, the flow control manifold 50, and the cylinders 5, is known to those in the art as a closed system. Therefore, any air, contained in the closed pressurized system must be removed. The said air removal is known as system bleeding to those in the art. The preferred method of bleeding the system is through as combination of moving the pressurized fluid through the pressurized system, which forces any air through the system and into the reservoir. After this is performed, the entire system is filled only with the pressurized fluid. The movement of the fluid is accomplished by alternately moving the pump handle 71 in an upwardly and downwardly motion. This said movement of the pump handle 71 causes the pump to push fluid through one of the hoses, through the flow control manifold 50, and into the lower cylinder fitting 7A. This causes the said fluid to flow underneath the piston 53 and begin forcing the piston 53 in an upwardly direction. As the piston 53 begins to rise, the fluid, resting above the piston 53 begins to be forced out of the upper cylinder fitting 7, through the pressure containing hose, connected to the upper cylinder fitting 7, through the flow control manifold 50, through the pump 61, and into the reservoir 59. This described flow and the accompanied rise of the piston 53 causes the cylinder shaft 13 to extract.

Turning the directional lever 79 ninety degrees from the position described in the above paragraph will cause the fluid to flow into the upper cylinder fitting 7 when the pump 61 is actuated by the moving the pump handle 71 in alternating upwardly and downwardly directions as described above. The said pump handle 71 movement causes the pump to push fluid through one of the hoses, through the flow control manifold 50, and into the upper cylinder fitting 7. This causes the said fluid to flow above the piston 53 and begin forcing the piston 53 in a downwardly direction. As the piston 53 begins to move in the said downward direction, the fluid, resting below the piston 53 begins to be forced out of the lower cylinder fitting 7A, through the pressure containing hose connected to the lower cylinder fitting 7A, through the flow control manifold 50, through the hand pump 40, and into the reservoir 59. This described flow of the fluid and the accompanied downward movement of the piston 53 causes the cylinder shaft 13 to retract.

In use, the single cylinder version of the present device produces an upward force on the pad eye or lifting lug when the cylinder shaft 13 retracts. Therefore, the directional lever 79 shall me moved into the position which causes the fluid to flow into the upper cylinder fitting 7.

In use, the double cylinder version of the present device produces an upward force on the pad eye or lifting lug when the cylinder shaft 13 extracts. Therefore, the directional lever 79 shall me moved into the position which causes the fluid to flow into the lower cylinder fitting 7A.

In use, the pressure gauge 73 will indicate the system pressure. As the pump handle 71 is moved, as described above, the pressure, indicated on the pressure gauge will increase. When the indicated pressure is approximately the same as the calculated pressure corresponding to the required test load, as described above, then the proper test load has been applied. It should be understood that this paragraph describes the operation regardless of the direction of fluid flow or the position of the directional valve handle 79.

In use, after the test is completed, the directional valve 79 should be turned ninety degrees, and the pump 61 should be actuated by the pump handle 71, as previously described, until the system pressure, as indicated by the gauge or other monitoring device, is completely relieved.

It should be appreciated that the directional lever 79 does not actually control flow but rather moves the directional valve 77 into a position that changes the flow direction. The detailed workings of the directional valve 77 is well known to those skilled in the art.

Figure 9:
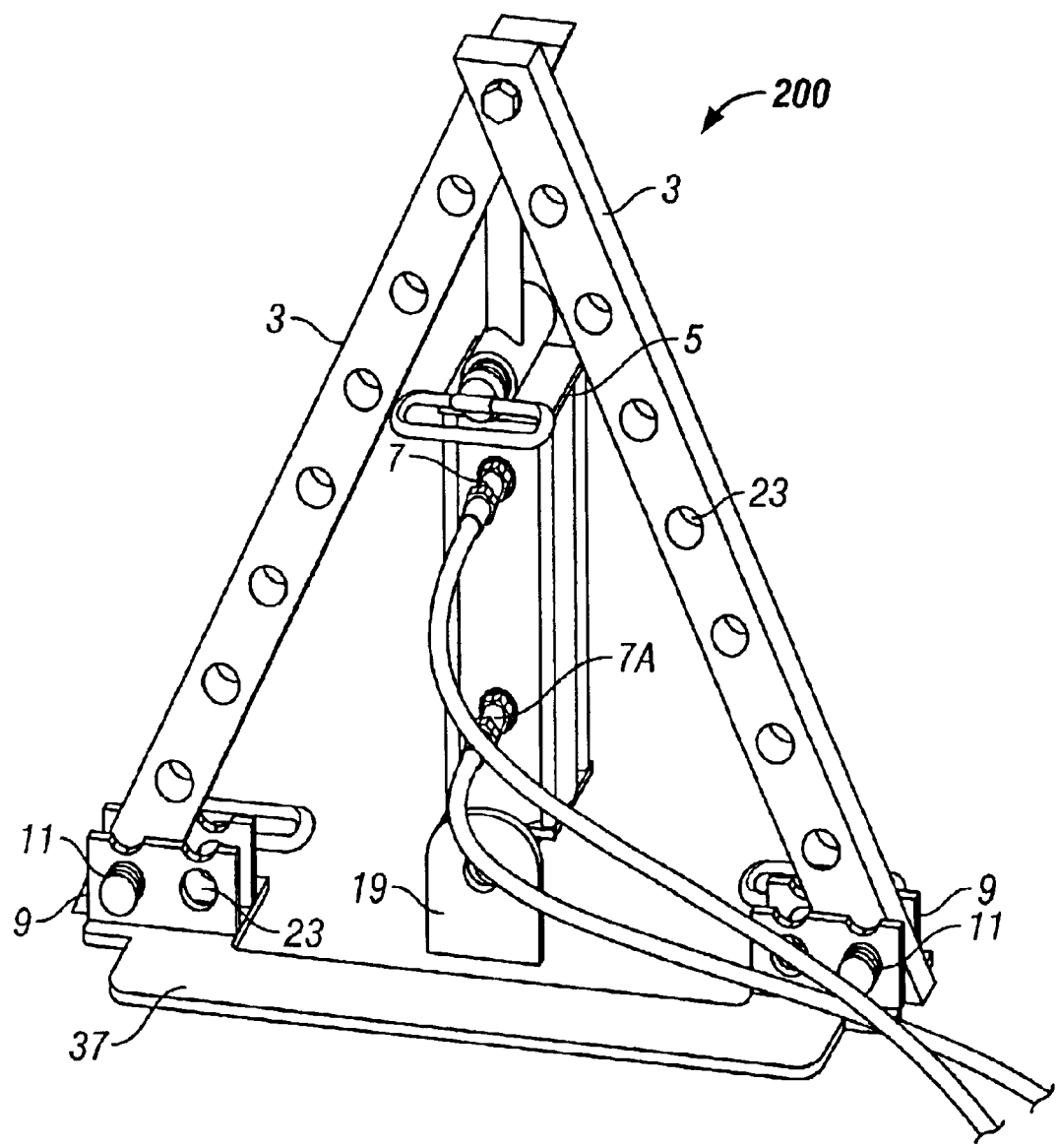
FIG. 9 is a front view assembly drawing of another alternative embodiment of the testing apparatus.
Figure 9A:
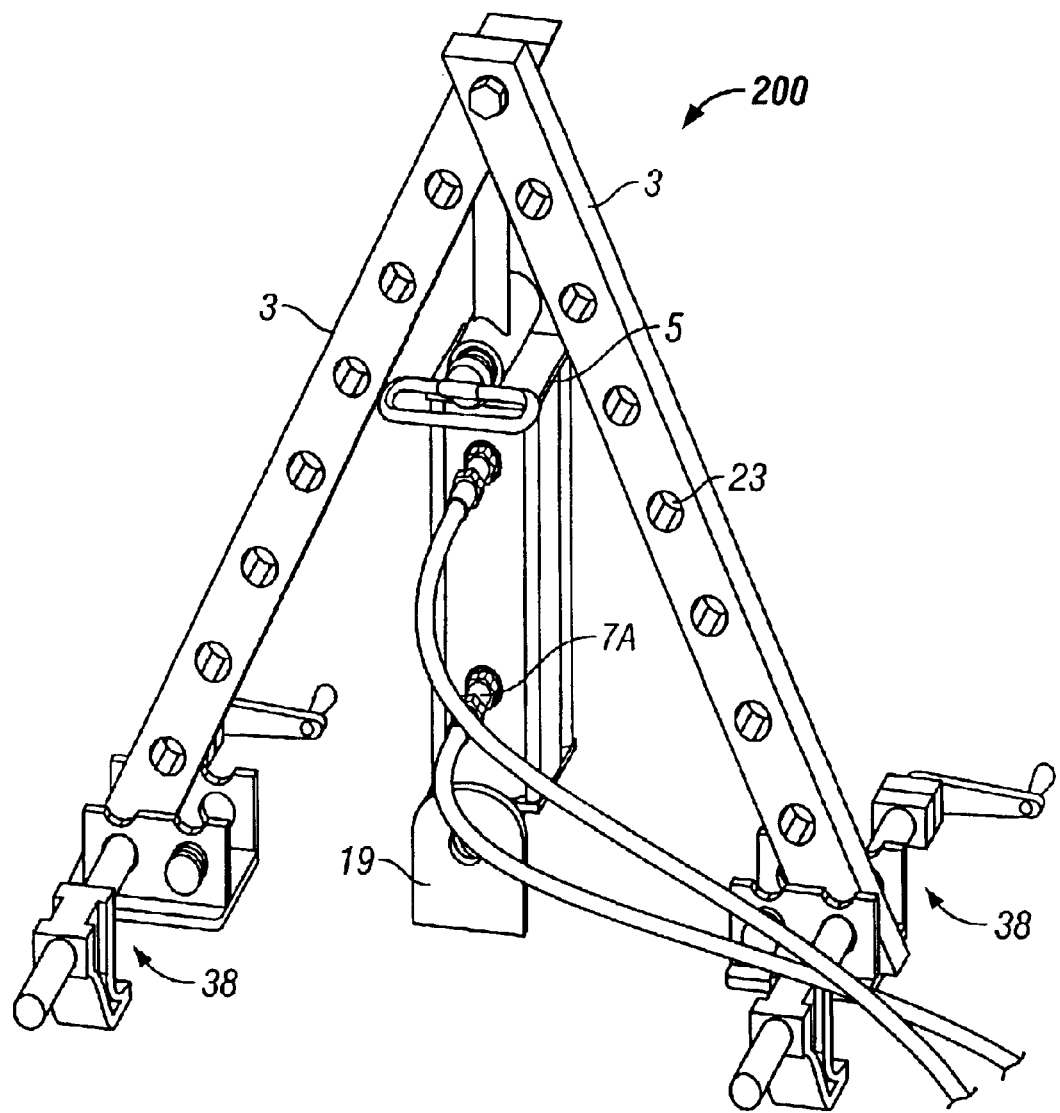
FIG. 9A is another embodiment of FIG. 9 illustrating the option of attachment, of the present apparatus, to the device to be tested, by clamps.

Those who are skilled in the art will readily perceive how to modify the present apparatus still further. For example, most of the illustrated connections utilize pins, however, it should be recognized that other methods of connection may be utilized, such as threaded connectors or if the unit will be modified for permanent installation as opposed to portable, the connections could be welded. Further, the frames or structures, of this apparatus, do not need to be comprised of substantially vertical and horizontal members. These members could be curved, angled, or joined in a manner to provide the substantially same function and substantially same result in testing the pad eye or other lifting lug attachment welds. FIGS. 8 and 9 illustrate two such modifications where the alternative embodiment consists of an A-frame structure and FIG. 8 illustrates a bridge plate or cross bar being used with the A-frame. FIGS. 8A and 9A show an alternative embodiment using clamps 38 for attachment to the base support structure to which the pad eye 19, the lifting lug, or other lifting connection is attached to. Additionally, there are other means of providing pressure to actuate the cylinders, other configurations for the pump equipment and associated hoses, as well as additional measuring and measurement recording devices which can all be used within and in conjunction with the present device. Further, other pressurized fluids can be used to actuate the cylinders. In addition, the subject matter of the present device would not be considered limited to a particular material of construction. Therefore, many materials of construction are contemplated by the present apparatus including but not limited to various metals or combinations of metals. As many possible embodiments maybe made of the present apparatus without departing from the scope thereof, it is to be understood that all matter herein set forth or shown in the accompanying drawings is to be interpreted as illustrative and not in a limiting sense.

What is claimed is:

1. An apparatus for testing the weld strength and integrity of an weld, comprising:
    a framework including a base, top, and side pieces;
    at least one fluid containing cylinder, mounted with the framework, for moving a piston therein inwardly and outwardly as fluid is moved out or in respectively; and
    structure for releaseably or permanently attaching to a pad eye or any device to be tested;
    whereby moving fluid into the cylinder causes the piston to move outwardly to tension the pad eye to testing the integrity of the welding in a non destructive manner.

2. The apparatus in claim 1, whereby moving fluid into the cylinder causes the piston to move inwardly to tension the pad eye then thereby testing the integrity of the weld.

3. The apparatus in claim 1, further including:
    a support beam having a top and bottom end; and
    a bridge plate or cross bar, having a left and right end, fixedly attached, on said left and right ends and near the center, to and supported by said beam or the cylinder.

4. The bridge plate or cross bar of claim 3, wherein said bridge plate can be comprised of two substantially identical plates wherein said cylinder shaft or support beams are fixedly attached and sandwiched between said bridge plates.

5. The apparatus in claim 3, wherein said bridge plate or cross bar can be curved.

6. The apparatus in claim 3, wherein said bridge plate or cross bar can be angled.

7. The apparatus of claim 1, wherein the cylinder further comprises:
    a first end and a second end;
    a substantially cylindrical piston carried in said cylinder for movement therein along an axis, of said cylinder, being substantially perpendicular to a plane formed between a pad eye or other lifting lug being tested and a weld attaching said pad eye or lifting lug to a base;
    a shaft, having a first end and a second end, the first end fixedly attached to said internal piston and said second end is fixedly attached to said bridge plate or cross bar; and
    first and second pressurized fluid attachment means;
    wherein said first pressurized fluid attachment means is disposed axially between said cylinder first end and said piston;
    wherein said second pressurized fluid attachment means is disposed axially between said cylinder second end and said piston; and
    wherein pressurized fluid enters said cylinder through said first attachment means or second attachment means.

8. The apparatus of claim 7, wherein said cylinder comprises:
    said second end of said shaft is fixedly attached to said pad eye or other device to be tested.

9. The apparatus in claim 1, further including:
    a control means for allowing pressurized fluid to be alternately supplied to and exhausted from said cylinder in a manner that the internal piston will move in an axial direction away from said first end of said cylinder, toward the second end of said cylinder, when the pressurized fluid enters through said first pressurized fluid attachment means, and that the said internal piston will move in an axial direction away from said second end of said cylinder toward the first end of said cylinder, when the pressurized fluid enters through said second pressurized fluid attachment means.

10. The apparatus in claim 9, wherein:
    the cylinder shaft will extend when said internal piston moves in an axial direction away from said first end of said cylinder toward the second end of said cylinder, causing said mounted cylinder to exert a force substantially perpendicular to a plane formed between a pad eye or other lifting lug being tested and a weld attaching said pad eye or lifting lug.

11. The apparatus of claim 9, wherein:
    the cylinder shaft will refract when said internal piston moves in an axial direction away from said second end of said cylinder toward said first end of said cylinder, causing said mounted cylinder to exert a force substantially perpendicular to a plane formed between a pad eye or other lifting lug being tested and a weld attaching said pad eye or lifting lug.

12. The apparatus in claim 1, wherein said mounted cylinder will exert a force substantially perpendicular to a plane formed between a pad eye or other lifting lug being tested and a weld attaching said pad eye or lifting lug creating a substantially perpendicular force away from said pad eye or other device being tested subjecting said attachment weld to a tension load.

13. A method for testing weld strength and integrity of an attachment weld when desired comprising the steps of:
- identifying a desired test piece wherein said test piece comprises a pad eye, lifting lug, or other device being tested;
- providing a framework including a base, top and side pieces;
- providing at least one fluid cylinder, having a first end and a second end, mounted with the framework, for moving a piston therein inwardly and outwardly as fluid is moved out or in respectively;
- providing a first and second attachment means, wherein a pressurized fluid can enter in or exhaust from said cylinder;
- providing an attachment structure for attaching externally to said test piece; and
- assembling the framework with the mounted cylinder fixedly attached at the first end of said cylinder externally to said test piece;
- whereby urging fluid into the cylinder causes the piston to move outwardly to tension the pad eye thus testing the integrity of the weld,
- whereby said testing is nondestructive; and
- whereby the testing technician or test operator can inspect the tested device and the weld for any structural damage or deformation.

14. The method as in claim 13, whereby urging fluid into the cylinder causes the piston to move inwardly to tension the test piece thus testing the integrity of the weld.

15. The method as in claim 13, wherein said framework is assembled at the location of the device to be tested.

16. The method as in claim 13, wherein the calculation of the required cylinder test pressure comprises the steps of:
- determining a required test load based on the weight to be supported, by the test piece;
- determining an effective area of the cylinder piston; and
- dividing said test load by the effective area of the cylinder piston.

17. The method as in claim 13, wherein:
- urging pressurized fluid is accomplished by a pumping device; and
- said urging of said pressurized fluid causes the cylinder piston to move in an axial direction away from said first end of said cylinder toward said second end of said cylinder, thereby causing the cylinder shaft to extract or causes the cylinder piston to move in an axial direction away from said second end of said cylinder toward said first end of said cylinder thereby causing the cylinder shaft to retract.

18. The method in claim 17, wherein:
- said cylinder piston moves in an axial direction away from said first end of said cylinder toward said second end of said cylinder when said pressurized fluid enters said cylinder through said first attachment means and the piston moves in an axial direction away from said second end of said cylinder toward said first end of said cylinder, when said pressurized fluid enters said cylinder through said second attachment means; and
- the entry, through said first attachment means or said second attachment means, of said pressurized fluid into said cylinder is controlled by a flow control manifold and a directional valve.

19. The method in claim 13 wherein the fluid pressure, in said cylinder, is determined at the control manifold and monitored by a pressure gauge.

20. A method for testing weld strength and integrity of an attachment weld when desired with a single cylinder apparatus comprising the steps of:
- identifying a desired test piece wherein said test piece comprises a pad eye, lifting lug, or other device being tested;
- providing a framework including a base, top and side pieces;
- providing at least one fluid cylinder, mounted with the framework, for moving a piston therein inwardly and outwardly as fluid is moved out or in respectively;
- providing an attachment structure for attaching external to said test piece;
- assembling the framework with the mounted cylinder fixedly attached at the first end of said cylinder external to said test piece;
- retracting the cylinder shaft thereby exerting a force substantially perpendicular to a plane formed between a pad eye or other lifting lug being tested and a weld attaching said pad eye or lifting lug to a base and away from said test piece;
- increasing said substantially perpendicular force by increasing the pressure of the pressurized fluid in the cylinder;
- increasing said pressure until the calculated required pressure is reached; and
- inspecting the test piece and its attachment weld for any structural damage or deformation;
- whereby increasing said substantially perpendicular force by increasing the pressure of the pressurized fluid in the cylinder is non-destructive in nature.

21. A method for testing weld strength and integrity of an attachment weld when desired with a multiple cylinder apparatus comprising the steps of:
- identifying a desired test piece wherein said test piece comprises a pad eye, lifting lug, or other device being tested;
- providing a framework including a base, top and side pieces;
- providing a plurality of fluid cylinders, each with a first and second end, mounted with the framework, for moving a piston therein, each said cylinder inwardly and outwardly as fluid is moved out or in respectively;
- providing an attachment structure for attaching externally to said test piece;
- assembling the framework with the mounted cylinders fixedly attached at the first end of said cylinders to said base and at said second end to a bridge plate or cross bar;
- extracting the cylinder shafts thereby exerting a force substantially perpendicular to and toward the bridge plate or cross bar;
- transferring said force from said bridge plate or cross bar to a support beam which is attached externally to the test piece;
- transferring said force from said support beam to said test piece;
- increasing said force by increasing the pressure of the pressurized fluid in the cylinder;
- increasing the pressure until the calculated required pressure is reached; and
- inspecting the test piece and its attachment weld for any structural damage or deformation;
- whereby increasing said force by increasing the pressure of the pressurized fluid in the cylinder is non-destructive in nature.

* * * * *

(12) EX PARTE REEXAMINATION CERTIFICATE (10455th)

United States Patent
Scarborough

(10) Number: US 6,848,322 C1
(45) Certificate Issued: Dec. 24, 2014

(54) APPARATUS AND METHOD FOR TESTING WELD INTEGRITY

(75) Inventor: Randall L. Scarborough, Carencrow, LA (US)

(73) Assignee: Randall L. Scarborough, Carencro, LA (US)

Reexamination Request:
No. 90/012,840, Aug. 7, 2013

Reexamination Certificate for:
Patent No.: 6,848,322
Issued: Feb. 1, 2005
Appl. No.: 10/365,105
Filed: Feb. 12, 2003

(51) Int. Cl.
*G01N 3/20* (2006.01)

(52) U.S. Cl.
USPC .............................................. 73/850

(58) Field of Classification Search
None
See application file for complete search history.

(56) References Cited

To view the complete listing of prior art documents cited during the proceeding for Reexamination Control Number 90/012,840, please refer to the USPTO's public Patent Application Information Retrieval (PAIR) system under the Display References tab.

*Primary Examiner* — Tuan H Nguyen

(57) ABSTRACT

An apparatus and method for testing weld integrity is disclosed which is portable, self-contained, adaptable for field use in most locations, and can verify the integrity of attachment welds. The testing apparatus includes a cylinder or cylinders, attachable to the desired object to be tested on one end and to a cross bar on the other end, support beam or beams which, along with the cylinder or cylinders, support the test apparatus, a supply for pressurized fluid, and a control manifold for flow direction and pressure measurement. The pressurized fluid moves the cylinder shaft creating a load on the test piece. As the fluid pressure increases the cylinder shafts extract or retract and exert a required load on the test piece. The test piece is then inspected for breakage or damage such as deformation or attachment weld cracking.

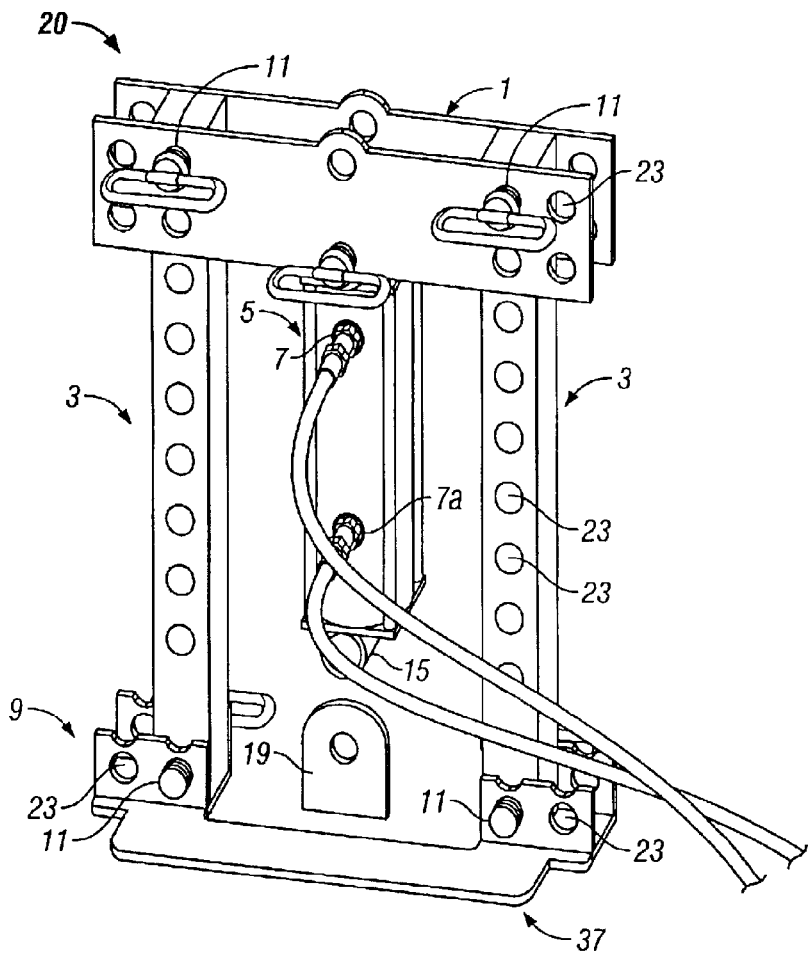

US 6,848,322 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 7, 8, 10-17 and 20-21 are determined to be patentable as amended.

Claims 3-6, 9, 18 and 19, dependent on an amended claim, are determined to be patentable.

1. An apparatus for testing the weld strength and integrity of an *attachment* weld, comprising:
   a framework including a base, top, and side pieces;
   at least one fluid containing cylinder, mounted with the framework, for moving a piston therein inwardly and outwardly as fluid is moved out or in respectively; and
   structure for releaseably or permanently attaching to a pad eye, *lifting lug* or [any] *other* device [to be tested] *joined by the attachment weld to another structure*;
   whereby moving fluid into the cylinder causes the piston to move outwardly to tension the pad eye, *lifting lug or other device* to [testing] *test* the integrity of the [welding] *attachment weld* in a [non destructive] *non-destructive* manner.

2. The apparatus in claim 1, whereby moving fluid into the cylinder causes the piston to move inwardly to tension the pad eye [then], *lifting lug or other device*, thereby testing the integrity of the *attachment* weld.

7. The apparatus of claim 1, wherein the cylinder further comprises:
   a first end and a second end;
   a substantially cylindrical piston carried in said cylinder for movement therein along an axis, of said cylinder, being substantially perpendicular to a plane formed between [a] *said* pad eye [or other], lifting lug [being tested] *or other device* and [a] *the attachment* weld attaching said pad eye [or], lifting lug *or other device* to [a base] *said another structure*;
   a shaft, having a first end and a second end, the first end fixedly attached to said internal piston and said second end is fixedly attached to said bridge plate or cross bar; and
   first and second pressurized fluid attachment means;
   wherein said first pressurized fluid attachment means is disposed axially between said cylinder first end and said piston;
   wherein said second pressurized fluid attachment means is disposed axially between said cylinder second end and said piston; and
   wherein pressurized fluid enters said cylinder through said first attachment means or second attachment means.

8. The apparatus of claim 7, wherein said cylinder comprises:
   said second end of said shaft is fixedly attached to said pad eye, *lifting lug,* or other device [to be tested].

10. The apparatus in claim 9, wherein:
    the cylinder shaft will extend when said internal piston moves in an axial direction away from said first end of said cylinder toward the second end of said cylinder, causing said mounted cylinder to exert a force substantially perpendicular to a plane formed between a *the* pad eye [lifting lug being tested], *lifting lug or other device* and a *the attachment* weld attaching said pad eye [or], lifting lug *or other device to said another structure*.

11. The apparatus of claim 9, wherein:
    the cylinder shaft will [refract] *retract* when said internal piston moves in an axial direction away from said second end of said cylinder toward said first end of said cylinder, causing said mounted cylinder to exert a force substantially perpendicular to a plane formed between [a] *said* pad eye, *lifting lug* or other [lifting lug being tested] *device* and a *the attachment* weld attaching said pad eye, *lifting lug* or [lifting lug] *other device to said another structure*.

12. The apparatus in claim 1, wherein said mounted cylinder will exert a force substantially perpendicular to a plane formed between [a] *the* pad eye, *lifting lug* or other device [lifting lug being tested] and [a] *said attachment* weld attaching said pad eye, *lifting lug* or *other* device [lifting lug] creating a substantially perpendicular force away from said pad eye, *lifting lug* or other device [being tested] subjecting said attachment weld to a tension load.

13. A method for testing weld strength and integrity of an attachment weld when desired comprising the steps of:
    identifying a desired [test piece wherein said test piece comprises] *attachment weld joining* a pad eye, lifting lug, or other device [being tested] *to another structure*;
    providing a framework including a base, top and side pieces;
    providing at least one fluid cylinder, having a first end and a second end, mounted with the framework, for moving a piston therein inwardly and outwardly as fluid is moved out or in respectively;
    providing a first and second attachment means, wherein a pressurized fluid can enter in or exhaust from said cylinder;
    providing an attachment structure for attaching externally to said [test piece] *pad eye, lifting lug or other device joined to said another structure by the attachment weld*; and
    assembling the framework with the mounted cylinder fixedly attached at the first end of said cylinder externally to said [test piece] *pad eye, lifting lug or other device joined to said another structure*;
    [whereby] urging fluid into the cylinder *to* causes the piston to move outwardly to tension the pad eye, *lifting lug or other device joined to said another structure* thus testing the integrity of the *attachment* weld,
    whereby said testing is nondestructive; and
    whereby [the] *a* testing technician or test operator can inspect the tested [device and the weld] *attachment weld and the pad eye, lifting lug or other device joined to another structure* for any structural damage or deformation.

14. The method as in claim 13, whereby urging fluid into the cylinder causes the piston to move inwardly to tension the [test piece] *pad eye, lifting lug or other device* thus testing the integrity of the weld.

15. The method as in claim 13, wherein said framework is assembled at the location of the [device] *weld* to be tested.

16. The method as in claim 13, wherein the calculation of the required cylinder test pressure comprises the steps of:

determining a required test load based on the weight to be supported, by the [test piece] *weld, pad eye, lifting lug or other device joined to the another structure by the weld to be tested*;

determining an effective area of the cylinder piston; and dividing said test load by the effective area of the cylinder piston.

17. The method as in claim 13, wherein:

urging pressurized fluid is accomplished by a pumping device; and said urging of said pressurized fluid causes the cylinder piston to move in an axial direction away from said first end of said cylinder toward said second end of said cylinder, thereby causing the cylinder shaft to extract or [causes] *causing* the cylinder piston to move in an axial direction away from said second end of said cylinder toward said first end of said cylinder thereby causing the cylinder shaft to retract.

20. A method for testing weld strength and integrity of an attachment weld when desired with a single cylinder apparatus comprising the steps of:

identifying a desired test piece wherein said test piece comprises *the attachment weld joining* a pad eye, lifting lug, or other device [being tested] *to another structure*;

providing a framework including a base, top and side pieces;

providing at least one fluid cylinder, mounted with the framework, for moving a piston therein inwardly and outwardly as fluid is moved out or in respectively;

providing an attachment structure for attaching external to said test piece;

assembling the framework with the mounted cylinder fixedly attached at the first end of said cylinder external to said test piece;

retracting the cylinder shaft thereby exerting a force substantially perpendicular to a plane formed between [a pad eye or other lifting lug being tested and a weld attaching said pad eye or lifting lug to a base and away from said test piece] *the attachment weld and the pad eye, lifting lug or other device joined to said another structure by the attachment weld*;

increasing said substantially perpendicular force by increasing the pressure of the pressurized fluid in the cylinder;

increasing said pressure until the calculated required pressure is reached; and inspecting the test piece [and its attachment weld] for any structural damage or deformation;

whereby increasing said substantially perpendicular force by increasing the pressure of the pressurized fluid in the cylinder is non-destructive in nature.

21. A method for testing weld strength and integrity of an attachment weld when desired with a multiple cylinder apparatus comprising the steps of:

identifying a [desired test piece wherein said test piece comprises] *weld joining* a pad eye, lifting lug, or other device [being tested] *to another structure*;

providing a framework including a base, top and side pieces;

providing a plurality of fluid cylinders, each with a first and second end, mounted with the framework, for moving a piston therein, each said cylinder inwardly and outwardly as fluid is moved out or in respectively;

providing an attachment structure for attaching externally to said [test piece] *pad eye, lifting lug, or other device joined to said another structure by the weld*;

assembling the framework with the mounted cylinders fixedly attached at the first end of said cylinders to said base and at said second end to a bridge plate or cross bar;

extracting the cylinder shafts thereby exerting a force substantially perpendicular to and toward the bridge plate or cross bar;

transferring said force from said bridge plate or cross bar to a support beam which is attached externally to the [test piece;] *pad eye, lifting lug, or other device joined to another structure by the weld*;

transferring said force from said support beam to said [test piece;] *pad eye, lifting lug, or other device joined to another structure by the weld*;

increasing said force by increasing the pressure of the pressurized fluid in the cylinder;

increasing the pressure until the calculated required pressure is reached; and inspecting the [test piece] *pad eye, lifting lug, or other device* and its attachment weld for any structural damage or deformation;

whereby increasing said force by increasing the pressure of the pressurized fluid in the cylinder is non-destructive in nature.

* * * * *